United States Patent
Nam et al.

(10) Patent No.: US 8,815,581 B2
(45) Date of Patent: Aug. 26, 2014

(54) METHOD FOR PROLIFERATING STEM CELLS BY ACTIVATING C-MET/HGF SIGNALING AND NOTCH SIGNALING

(75) Inventors: Do Hyun Nam, Sungnam-si (KR); Seung Chyul Hong, Seoul (KR); Bong gu Kang, Seoul (KR); Kyeung Min Joo, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 0 days.

(21) Appl. No.: 13/577,092

(22) PCT Filed: Feb. 1, 2011

(86) PCT No.: PCT/KR2011/000730
§ 371 (c)(1),
(2), (4) Date: Aug. 3, 2012

(87) PCT Pub. No.: WO2011/096728
PCT Pub. Date: Aug. 11, 2011

(65) Prior Publication Data
US 2012/0295348 A1     Nov. 22, 2012

(30) Foreign Application Priority Data

Feb. 3, 2010   (KR) .................. 10-2010-0010116
Feb. 3, 2010   (KR) .................. 10-2010-0010117

(51) Int. Cl.
*C12N 15/85*     (2006.01)
*C12N 15/63*     (2006.01)
*C12N 5/0797*     (2010.01)
*A61K 35/30*     (2006.01)

(52) U.S. Cl.
CPC .......... *C12N 5/0623* (2013.01); *C12N 2510/00* (2013.01); *C12N 2501/42* (2013.01); *A61K 35/30* (2013.01)
USPC ...................................... 435/325; 435/320.1

(58) Field of Classification Search
USPC .............................................. 435/325, 320.1
See application file for complete search history.

(56) References Cited

FOREIGN PATENT DOCUMENTS

KR    1020090008155 A    1/2009
KR    1020090129657 A    12/2009

OTHER PUBLICATIONS

Madonna et al (Basic Res Cardiol, 105: 443-452, 2010).*
Dezawa, et al., "Specific induction of neuronal cells from bone marrow stromal cells and application for autologous transplantation," The Journal of Clinical Investigation, vol. 113, No. 12, pp. 1701-1710, 2004.
GenBank BC130420. 1, *Homo sapiens* met proto-oncogene (HGF receptor), mRNA, complete cds, 2007.
Kokuzawa, et al., "Hepatocyte growth factor promotes proliferation and neuronal differentiation of neural stem cells from mouse embryos," Molecular and Cellular Neurscience, vol. 24, No. 1, pp. 190-197, 2003.
Ma, et al., "c-MET Mutational Analysis in Small Cell Lung Cancer: Novel Juxtamembrane Domain Mutations Regulating Cytoskeletal Functions," Cancer Research, vol. 63, pp. 6272-6281, 2003.
Andreas Androutsellis-Theotokis, et al., Notch Signalling Regulates Stem Cell Numbers In Vitro and In Vivo, Nature Publishing Group, vol. 442, No. 17, 2006.
Jieli Chen, et al., Atorvastatin Promotes Presenilin-1 Expression and Notch ! . . . , Journal of the American Heart Association, Stroke, 39, pp. 220-226, 2008.
Hayase et al., Committed neural progenitor cells derived from genetically modified bone marrow stromal cells ameliorate deficits in a rat model of stroke, Journal of Cerebral Blood Flow & Metabolism, May 13, 2009, vol. 29, 1409-1420.
Rodriguez-Rivera et al., Activated Notch 1 is a stronger astrocytic stimulus than leukemia inhibitory factor for rat neural stem cells, Int. J. Dev. Biol., Mar. 5, 2009, vol. 53: 947-953.
Yasuhara et al, Notch-induced rat and human bone marrow stromal cell grafts reduce ischemic cell loss and ameliorate behavioral deficits in chronic stroke animals, Stem Cells and Development, Dec. 2009, vol. 18, No. 10, 1501-1514.
Woo et al, Notch signaling is required for maintaining stem-cell features of neuroprogenitor cells derived from human embryonic stem cells, BMC Neuroscience, Aug. 17, 2009, vol. 10, No. 1, 97-109.
Extended European Search Report, Sep. 17, 2013.

* cited by examiner

*Primary Examiner* — Marcia S Noble
*Assistant Examiner* — Magdalene Sgagias
(74) *Attorney, Agent, or Firm* — Lucas & Mercanti, LLP

(57) ABSTRACT

The present invention relates to stem cells in which a gene that activates signaling is introduced and to a method for proliferating the stem cells. More specifically, the invention relates to a method of significantly increasing the ability of stem cells to proliferate, either by transfecting stem cells with the Notch intracellular domain (NICD) to activate the Notch signaling pathway, or by transfecting stem cells with the c-MET gene and treating the transfected stem cells with the HGF ligand protein to activate the c-MET/HGF signaling pathway. According to the present invention, as a result of activating the Notch signaling pathway or the c-MET/HGF signaling pathway, stem cells having an excellent ability to proliferate can be produced in large amounts. Particularly, since neural stem cells which have been difficult to culture in vitro can be proliferated in large amounts, thus the neural stem cells will be more useful for the preparation of cell therapeutic agents for treating cranial nerve diseases.

6 Claims, 3 Drawing Sheets

SEQUENCE LISTING

<160> NUMBER OF SEQ ID NOS: 8

<210> SEQ ID NO 1
<211> LENGTH: 2395
<212> TYPE: DNA
<213> ORGANISM: Homo sapiens

<400> SEQUENCE: 1

```
caccatgcgg cggcagcatg gccagctctg gttccctgag ggcttcaaag tgtctgaggc    60
cagcaagaag aagcggcggg agcccctcgg cgaggactcc gtgggcctca gcccctgaa   120
gaacgcttca gacggtgccc tcatggacga caaccagaat gagtgggggg acgaggacct   180
ggagaccaag aagttccggt tcgaggagcc cgtggttctg cctgacctgg acgaccagac   240
agaccaccgg cagtggactc agcagcacct ggatgccgct gacctgcgca tgtctgccat   300
ggccccccaca ccgccccagg gtgaggttga cgccgactgc atggacgtca atgtccgcgg   360
gcctgatggc ttcaccccgc tcatgatcgc ctcctgcagc gggggcggcc tggagacggg   420
caacagcgag gaagaggagg acgcgccggc cgtcatctcc gacttcatct accagggcgc   480
cagcctgcac aaccagacag accgcacggg cgagaccgcc ttgcacctgg ccgcccgcta   540
ctcacgctct gatgccgcca gcgcctgct ggaggccagc gcagatgcca acatccagga   600
caacatgggc cgcacccccgc tgcatgcggc tgtgtctgcc gacgcacaag gtgtcttcca   660
gatcctgatc cggaaccgag ccacagacct ggatgcccgc atgcatgatg gcacgacgcc   720
actgatcctg gctgcccgcc tggccgtgga gggcatgctg gaggacctca tcaactcaca   780
cgccgacgtc aacgccgtag atgacctggg caagtccgcc ctgcactggg ccgccgccgt   840
gaacaatgtg gatgccgcag ttgtgctcct gaagaacggg gctaacaaag atatgcagaa   900
caacagggag gagacacccc tgtttctggc cgcccgggag ggcagctacg agaccgccaa   960
ggtgctgctg gaccactttg ccaaccggga catcacggat catatggacc gcctgccgcg  1020
cgacatcgca caggagcgca tgcatcacga catcgtgagg ctgctggacg agtacaacct  1080
ggtgcgcagc ccgcagctgc acggagcccc gctgggggc acgccacccc tgtcgccccc  1140
gctctgctcg cccaacggct acctgggcag cctcaagccc ggcgtgcagg caagaaggt  1200
ccgcaagccc agcagcaaag gcctggcctg tggaagcaag gaggccaagg acctcaaggc  1260
acggaggaag aagtcccagg acggcaaggg ctgcctgctg gacagctccg gcatgctctc  1320
gcccgtggac tccctggagt caccccatgg ctacctgtca gacgtggcct cgccgccact  1380
gctgccctcc ccgttccagc agtctccgtc cgtgcccctc aaccacctgc ctgggatgcc  1440
cgacacccac ctgggcatcg gcacctgaa cgtggcggcc aagcccgaga tggcggcgct  1500
gggtggggc ggccggctgg cctttgagac tggcccacct cgtctctccc acctgcctgt  1560
ggcctctggc accagcaccg tcctgggctc agcagcgga ggggccctga atttcactgt  1620
gggcgggtcc accagtttga atggtcaatg cgagtggctg tcccggctgc agagcggcat  1680
ggtgccgaac caatacaacc ctctgcgggg gagtgtggca ccaggccccc tgagcacaca  1740
ggccccctcc ctgcagcatg gcatggtagg cccgctgcac agtagccttg ctgccagcgc  1800
cctgtcccag atgatgagct accagggcct gccagcacc cggctggcca cccagcctca  1860
cctggtgcag acccagcagg tgcagccaca aaacttacag atgcagcagc agaacctgca  1920
gccagcaaac atccagcagc agcaaagcct gcagccgcca ccaccaccac acagccgca  1980
ccttggcgtg agctcagcag ccagcggcca cctggccgg agcttcctga gtggagagcc  2040
gagccaggca gacgtgcagc cactgggccc cagcagcctg cgcgtgcaca ctattctgcc  2100
ccaggagagc cccgccctgc ccacgtcgct gccatcctcg ctggtccac ccgtgaccgc  2160
agcccagttc ctgacgcccc cctcgcagca cagctactcc tcgcctgtgg acaacacccc  2220
cagccaccag ctacaggtgc ctgagcaccc cttcctcacc ccgtcccctg agtcccctga  2280
ccagtggtcc agctcgtccc cgcattccaa cgtctccgac tggtccgagg gcgtctccag  2340
```

```
ccctcccacc agcatgcagt cccagatcgc ccgcattccg gaggccttca agtaa           2395
```

<210> SEQ ID NO 2
<211> LENGTH: 795
<212> TYPE: PRT
<213> ORGANISM: Homo sapiens

<400> SEQUENCE: 2

```
Arg Arg Gln His Gly Gln Leu Trp Phe Pro Glu Gly Phe Lys Val Ser
  1               5                  10                  15

Glu Ala Ser Lys Lys Arg Arg Glu Pro Leu Gly Glu Asp Ser Val
             20                  25                  30

Gly Leu Lys Pro Leu Lys Asn Ala Ser Asp Gly Ala Leu Met Asp Asp
         35                  40                  45

Asn Gln Asn Glu Trp Gly Asp Glu Asp Leu Glu Thr Lys Lys Phe Arg
     50                  55                  60

Phe Glu Glu Pro Val Val Leu Pro Asp Leu Asp Asp Gln Thr Asp His
 65                  70                  75                  80

Arg Gln Trp Thr Gln Gln His Leu Asp Ala Ala Asp Leu Arg Met Ser
                 85                  90                  95

Ala Met Ala Pro Thr Pro Pro Gln Gly Glu Val Asp Ala Asp Cys Met
            100                 105                 110

Asp Val Asn Val Arg Gly Pro Asp Gly Phe Thr Pro Leu Met Ile Ala
        115                 120                 125

Ser Cys Ser Gly Gly Gly Leu Glu Thr Gly Asn Ser Glu Glu Glu Glu
    130                 135                 140

Asp Ala Pro Ala Val Ile Ser Asp Phe Ile Tyr Gln Gly Ala Ser Leu
145                 150                 155                 160

His Asn Gln Thr Asp Arg Thr Gly Glu Thr Ala Leu His Leu Ala Ala
                165                 170                 175

Arg Tyr Ser Arg Ser Asp Ala Ala Lys Arg Leu Leu Glu Ala Ser Ala
            180                 185                 190

Asp Ala Asn Ile Gln Asp Asn Met Gly Arg Thr Pro Leu His Ala Ala
        195                 200                 205

Val Ser Ala Asp Ala Gln Gly Val Phe Gln Ile Leu Ile Arg Asn Arg
    210                 215                 220

Ala Thr Asp Leu Asp Ala Arg Met His Asp Gly Thr Thr Pro Leu Ile
225                 230                 235                 240

Leu Ala Ala Arg Leu Ala Val Glu Gly Met Leu Glu Asp Leu Ile Asn
                245                 250                 255

Ser His Ala Asp Val Asn Ala Val Asp Asp Leu Gly Lys Ser Ala Leu
            260                 265                 270

His Trp Ala Ala Ala Val Asn Asn Val Asp Ala Val Val Leu Leu
        275                 280                 285

Lys Asn Gly Ala Asn Lys Asp Met Gln Asn Asn Arg Glu Glu Thr Pro
    290                 295                 300

Leu Phe Leu Ala Ala Arg Glu Gly Ser Tyr Glu Thr Ala Lys Val Leu
305                 310                 315                 320

Leu Asp His Phe Ala Asn Arg Asp Ile Thr Asp His Met Asp Arg Leu
                325                 330                 335

Pro Arg Asp Ile Ala Gln Glu Arg Met His His Asp Ile Val Arg Leu
            340                 345                 350

Leu Asp Glu Tyr Asn Leu Val Arg Ser Pro Gln Leu His Gly Ala Pro
        355                 360                 365
```

-continued

```
Leu Gly Gly Thr Pro Thr Leu Ser Pro Pro Leu Cys Ser Pro Asn Gly
    370                 375                 380
Tyr Leu Gly Ser Leu Lys Pro Gly Val Gln Gly Lys Lys Val Arg Lys
385                 390                 395                 400
Pro Ser Ser Lys Gly Leu Ala Cys Gly Ser Lys Glu Ala Lys Asp Leu
                405                 410                 415
Lys Ala Arg Arg Lys Lys Ser Gln Asp Gly Lys Gly Cys Leu Leu Asp
                420                 425                 430
Ser Ser Gly Met Leu Ser Pro Val Asp Ser Leu Glu Ser Pro His Gly
                435                 440                 445
Tyr Leu Ser Asp Val Ala Ser Pro Pro Leu Leu Pro Ser Pro Phe Gln
450                 455                 460
Gln Ser Pro Ser Val Pro Leu Asn His Leu Pro Gly Met Pro Asp Thr
465                 470                 475                 480
His Leu Gly Ile Gly His Leu Asn Val Ala Ala Lys Pro Glu Met Ala
                485                 490                 495
Ala Leu Gly Gly Gly Arg Leu Ala Phe Glu Thr Gly Pro Pro Arg
                500                 505                 510
Leu Ser His Leu Pro Val Ala Ser Gly Thr Ser Thr Val Leu Gly Ser
            515                 520                 525
Ser Ser Gly Gly Ala Leu Asn Phe Thr Val Gly Gly Ser Thr Ser Leu
530                 535                 540
Asn Gly Gln Cys Glu Trp Leu Ser Arg Leu Gln Ser Gly Met Val Pro
545                 550                 555                 560
Asn Gln Tyr Asn Pro Leu Arg Gly Ser Val Ala Pro Gly Pro Leu Ser
                565                 570                 575
Thr Gln Ala Pro Ser Leu Gln His Gly Met Val Gly Pro Leu His Ser
                580                 585                 590
Ser Leu Ala Ala Ser Ala Leu Ser Gln Met Met Ser Tyr Gln Gly Leu
            595                 600                 605
Pro Ser Thr Arg Leu Ala Thr Gln Pro His Leu Val Gln Thr Gln Gln
            610                 615                 620
Val Gln Pro Gln Asn Leu Gln Met Gln Gln Asn Leu Gln Pro Ala
625                 630                 635                 640
Asn Ile Gln Gln Gln Ser Leu Gln Pro Pro Pro Pro Gln
                645                 650                 655
Pro His Leu Gly Val Ser Ser Ala Ala Ser Gly His Leu Gly Arg Ser
                660                 665                 670
Phe Leu Ser Gly Glu Pro Ser Gln Ala Asp Val Gln Pro Leu Gly Pro
            675                 680                 685
Ser Ser Leu Ala Val His Thr Ile Leu Pro Gln Glu Ser Pro Ala Leu
690                 695                 700
Pro Thr Ser Leu Pro Ser Ser Leu Val Pro Pro Val Thr Ala Ala Gln
705                 710                 715                 720
Phe Leu Thr Pro Pro Ser Gln His Ser Tyr Ser Ser Pro Val Asp Asn
                725                 730                 735
Thr Pro Ser His Gln Leu Gln Val Pro Glu His Pro Phe Leu Thr Pro
                740                 745                 750
Ser Pro Glu Ser Pro Asp Gln Trp Ser Ser Ser Ser Pro His Ser Asn
                755                 760                 765
Val Ser Asp Trp Ser Glu Gly Val Ser Ser Pro Pro Thr Ser Met Gln
770                 775                 780
Ser Gln Ile Ala Arg Ile Pro Glu Ala Phe Lys
```

<210> SEQ ID NO 3
<211> LENGTH: 25
<212> TYPE: DNA
<213> ORGANISM: Artificial Sequence
<220> FEATURE:
<223> OTHER INFORMATION: NICD sense primer

<400> SEQUENCE: 3
caccatgcgg cggcagcatg gccag                                           25

<210> SEQ ID NO 4
<211> LENGTH: 22
<212> TYPE: DNA
<213> ORGANISM: Artificial Sequence
<220> FEATURE:
<223> OTHER INFORMATION: NICD anti-sense primer

<400> SEQUENCE: 4
ttacttgaag gcctccggaa tg                                              22

<210> SEQ ID NO 5
<211> LENGTH: 4173
<212> TYPE: DNA
<213> ORGANISM: Homo sapiens

<400> SEQUENCE: 5

```
atgaaggccc ccgctgtgct tgcacctggc atcctcgtgc tcctgtttac cttggtgcag      60
aggagcaatg gggagtgtaa agaggcacta gcaaagtccg agatgaatgt gaatatgaag     120
tatcagcttc ccaacttcac cgcggaaaca cccatccaga atgtcattct acatgagcat     180
cacattttcc ttggtgccac taactacatt tatgttttaa atgaggaaga ccttcagaag     240
gttgctgagt acaagactgg gcctgtgctg aacacccag attgtttccc atgtcaggac     300
tgcagcagca aagccaattt atcaggaggt gtttggaaag ataacatcaa catggctcta     360
gttgtcgaca cctactatga tgatcaactc attagctgtg gcagcgtcaa cagagggacc     420
tgccagcgac atgtctttcc ccacaatcat actgctgaca tacagtcgga ggttcactgc     480
atattctccc cacagataga gagcccagc cagtgtcctg actgtgtggt gagcgccctg     540
ggagccaaag tcctttcatc tgtaaaggac cggttcatca acttctttgt aggcaatacc     600
ataaattctt cttatttccc agatcatcca ttgcattcga tatcagtgag aaggctaaag     660
gaaacgaaag atggttttat gttttttgacg gaccagtcct acattgatgt tttacctgag     720
ttcagagatt cttaccccat taagtatgtc catgcctttg aaagcaacaa ttttatttac     780
ttcttgacgg tccaaaggga aactctagat gctcagactt tcacacaag aataatcagg     840
ttctgttcca taaactctgg attgcattcc tacatggaaa tgcctctgga gtgtattctc     900
acagaaaaga gaaaaagag atccacaaag aaggaagtgt taatatact tcaggctgcg     960
tatgtcagca agcctggggc ccagcttgct agacaaatag gagccagcct gaatgatgac    1020
attcttttcg gggtgttcgc acaaagcaag ccagattctg ccgaaccaat ggatcgatct    1080
gccatgtgtg cattccctat caaatatgtc aacgacttct caacaagat cgtcaacaaa    1140
aacaatgtga gatgtctcca gcatttttac ggacccaatc atgagcactg ctttaatagg    1200
acacttctga aaattcatc aggctgtgaa gcgcgccgtg atgaatatcg aacagagttt    1260
accacagctt tgcagcgcgt tgacttattc atgggtcaat tcagcgaagt cctcttaaca    1320
tctatatcca ccttcattaa aggagacctc accatagcta atcttgggac atcagagggt    1380
```

```
cgcttcatgc aggttgtggt ttctcgatca ggaccatcaa cccctcatgt gaattttctc    1440
ctggactccc atccagtgtc tccagaagtg attgtggagc atacattaaa ccaaaatggc    1500
tacacactgg ttatcactgg gaagaagatc acgaagatcc cattgaatgg cttgggctgc    1560
agacatttcc agtcctgcag tcaatgcctc tctgccccac cctttgttca gtgtggctgg    1620
tgccacgaca aatgtgtgcg atcggaggaa tgcctgagcg ggacatggac tcaacagatc    1680
tgtctgcctg caatctacaa ggttttccca aatagtgcac cccttgaagg agggacaagg    1740
ctgaccatat gtggctggga ctttggattt cggaggaata taaatttga tttaaagaaa    1800 actagagttc tccttggaaa tgagagctgc accttgactt taagtgagag cacgatgaat    1860
acattgaaat gcacagttgg tcctgccatg aataagcatt tcaatatgtc cataattatt    1920
tcaaatggcc acgggacaac acaatacagt acattctcct atgtggatcc tgtaataaca    1980
agtatttcgc cgaaatacgg tcctatggct ggtggcactt tacttacttt aactggaaat    2040
tacctaaaca gtgggaattc tagacacatt tcaattggtg gaaaaacatg tactttaaaa    2100
agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatctttta ttagtggtgg gagcacaata    2280
acaggtgttg ggaaaaacct gaattcagtt agtgtcccga gaatggtcat aaatgtgcat    2340
gaagcaggaa ggaactttac agtggcatgt caacatcgct ctaattcaga gataatctgt    2400
tgtaccactc cttccctgca acagctgaat ctgcaactcc ccctgaaaac caaagccttt    2460
ttcatgttag atgggatcct ttccaaatac tttgatctca tttatgtaca taatcctgtg    2520 tttaagccctt tgaaaagcc agtgatgatc tcaatgggca atgaaaatgt actggaaatt    2580
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacaggat tgattgctgg tgttgtctca    2820
atatcaacag cactgttatt actacttggg ttttcctgt ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacgac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat gtgcatttc    3240 aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga atgagagactc ataatccaac tgtaaaagat    3540
cttattggct ttggtcttca gtagccaaa ggcatgaaat atcttgcaag caaaaagttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
```

-continued

| | |
|---|---|
| acaggtgcaa agctgccagt gaagtggatg gctttggaaa gtctgcaaac tcaaaagttt | 3780 |
| accaccaagt cagatgtgtg gtcctttggc gtgctcctct gggagctgat gacaagagga | 3840 |
| gccccacctt atcctgacgt aaacaccttt gatataactg tttacttgtt gcaagggaga | 3900 |
| agactcctac aacccgaata ctgcccagac cccttatatg aagtaatgct aaaatgctgg | 3960 |
| caccctaaag ccgaaatgcg cccatccttt tctgaactgg tgtcccggat atcagcgatc | 4020 |
| ttctctactt tcattgggga gcactatgtc catgtgaacg ctacttatgt gaacgtaaaa | 4080 |
| tgtgtcgctc cgtatccttc tctgttgtca tcagaagata cgctgatga tgaggtggac | 4140 |
| acacgaccag cctccttctg ggagacatca tag | 4173 |

<210> SEQ ID NO 6
<211> LENGTH: 1390
<212> TYPE: PRT
<213> ORGANISM: Homo sapiens

<400> SEQUENCE: 6

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg

```
                    290                 295                 300
Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
                370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
                450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
                530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
                610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
                690                 695                 700

Ser Ile Leu Glu Cys Tyr Thr Pro Ala Gln Thr Ile Ser Thr Glu Phe
705                 710                 715                 720
```

-continued

```
Ala Val Lys Leu Lys Ile Asp Leu Ala Asn Arg Glu Thr Ser Ile Phe
            725                 730                 735

Ser Tyr Arg Glu Asp Pro Ile Val Tyr Glu Ile His Pro Thr Lys Ser
        740                 745                 750

Phe Ile Ser Gly Gly Ser Thr Ile Thr Gly Val Gly Lys Asn Leu Asn
            755                 760             765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
        850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
            965                 970                 975

Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
        995                 1000                1005

Glu Asp Gln Phe Pro Asn Ser Ser Gln Asn Gly Ser Cys Arg Gln Val
        1010                1015                1020

Gln Tyr Pro Leu Thr Asp Met Ser Pro Ile Leu Thr Ser Gly Asp Ser
1025                1030                1035                1040

Asp Ile Ser Ser Pro Leu Leu Gln Asn Thr Val His Ile Asp Leu Ser
                1045                1050                1055

Ala Leu Asn Pro Glu Leu Val Gln Ala Val Gln His Val Val Ile Gly
            1060                1065                1070

Pro Ser Ser Leu Ile Val His Phe Asn Glu Val Ile Gly Arg Gly His
                1075                1080                1085

Phe Gly Cys Val Tyr His Gly Thr Leu Leu Asp Asn Asp Gly Lys Lys
        1090                1095                1100

Ile His Cys Ala Val Lys Ser Leu Asn Arg Ile Thr Asp Ile Gly Glu
1105                1110                1115                1120

Val Ser Gln Phe Leu Thr Glu Gly Ile Ile Met Lys Asp Phe Ser His
                1125                1130                1135
```

```
Pro Asn Val Leu Ser Leu Leu Gly Ile Cys Leu Arg Ser Glu Gly Ser
                1140                1145                1150

Pro Leu Val Val Leu Pro Tyr Met Lys His Gly Asp Leu Arg Asn Phe
        1155                1160                1165

Ile Arg Asn Glu Thr His Asn Pro Thr Val Lys Asp Leu Ile Gly Phe
    1170                1175                1180

Gly Leu Gln Val Ala Lys Gly Met Lys Tyr Leu Ala Ser Lys Lys Phe
1185                1190                1195                1200

Val His Arg Asp Leu Ala Ala Arg Asn Cys Met Leu Asp Glu Lys Phe
                1205                1210                1215

Thr Val Lys Val Ala Asp Phe Gly Leu Ala Arg Asp Met Tyr Asp Lys
                1220                1225                1230

Glu Tyr Tyr Ser Val His Asn Lys Thr Gly Ala Lys Leu Pro Val Lys
        1235                1240                1245

Trp Met Ala Leu Glu Ser Leu Gln Thr Gln Lys Phe Thr Thr Lys Ser
    1250                1255                1260

Asp Val Trp Ser Phe Gly Val Leu Leu Trp Glu Leu Met Thr Arg Gly
1265                1270                1275                1280

Ala Pro Pro Tyr Pro Asp Val Asn Thr Phe Asp Ile Thr Val Tyr Leu
                1285                1290                1295

Leu Gln Gly Arg Arg Leu Leu Gln Pro Glu Tyr Cys Pro Asp Pro Leu
                1300                1305                1310

Tyr Glu Val Met Leu Lys Cys Trp His Pro Lys Ala Glu Met Arg Pro
                1315                1320                1325

Ser Phe Ser Glu Leu Val Ser Arg Ile Ser Ala Ile Phe Ser Thr Phe
    1330                1335                1340

Ile Gly Glu His Tyr Val His Val Asn Ala Thr Tyr Val Asn Val Lys
1345                1350                1355                1360

Cys Val Ala Pro Tyr Pro Ser Leu Leu Ser Ser Glu Asp Asn Ala Asp
                1365                1370                1375

Asp Glu Val Asp Thr Arg Pro Ala Ser Phe Trp Glu Thr Ser
                1380                1385                1390

<210> SEQ ID NO 7
<211> LENGTH: 29
<212> TYPE: DNA
<213> ORGANISM: Artificial Sequence
<220> FEATURE:
<223> OTHER INFORMATION: c-MET Sense primer

<400> SEQUENCE: 7
caccggtacc atgaaggccc ccgctgtgc                                    29

<210> SEQ ID NO 8
<211> LENGTH: 31
<212> TYPE: DNA
<213> ORGANISM: Artificial Sequence
<220> FEATURE:
<223> OTHER INFORMATION: c-MET AntiSense primer

<400> SEQUENCE: 8
gcggccgcct atgatgtctc ccagaaggag g                                 31
```

METHOD FOR PROLIFERATING STEM CELLS BY ACTIVATING C-MET/HGF SIGNALING AND NOTCH SIGNALING

CROSS-REFERENCE TO RELATED APPLICATIONS

This application is a 371 of PCT/KR2011/000730, filed Feb. 1, 2011, which claims the benefit of Korean Patent Application Nos. KR 10-2010-0010117, filed Feb. 3, 2010 and KR 10-2010-0010116, filed Feb. 3, 2010, the contents of each of which are incorporated herein by reference.

TECHNICAL FIELD

The present invention relates to stem cells in which a gene that activates signaling is introduced and a method for proliferating the stem cells, and more particularly to a method of significantly increasing the ability of stem cells to proliferate, either by transfecting stem cells with the Notch intracellular domain (NICD) to activate the Notch signaling pathway, or by transfecting stem cells with the c-MET gene and treating the transfected stem cells with the HGF ligand protein to activate the c-MET/HGF signaling pathway.

BACKGROUND ART

Biotechnology in the 21$^{st}$ century presents the possibility of new solutions to food, environmental and health problems, with the ultimate object of promoting human prosperity. In recent years, the technology of using stem cells has been considered as a new way to treat incurable diseases. Previously, organ transplantation, gene therapy, etc., were presented for the treatment of incurable human diseases, but their efficient use has not been achieved due to immune rejection, short supply of organs, insufficient development of vectors, and an insufficient knowledge of disease genes.

With increasing interests in stem cell studies, it has been recognized that totipotent stem cells having the ability to form all the organs by proliferation and differentiation can not only treat most of diseases but also fundamentally heal organ injuries. Stem cells refer to cells having not only self-replication ability but also the ability to differentiate into at least two cells, and can be divided into totipotent stem cells, pluripotent stem cells, and multipotent stem cells. Many scientists have suggested clinical applicability of stem cells for the regeneration of all the organs and the treatment of incurable diseases, including Parkinson's disease, various cancers, diabetes and spinal damages.

Particularly, neural stem cells are capable of self-renewal and have the potential to differentiate into three major cell types of the central nerve system, including neurons, astrocytes, and oligodendrocytes. Accordingly, interests in neural stem cells are increasing recently, not only with regard to basic researches on mechanisms of proliferation and differentiation of stem cells and development of nervous systems, but also with regard to the possibility of new cell and gene therapy in neurological diseases, which are known not to be regulated once damaged, utilizing biological characteristics of the neural stem cells.

The concept that stem cells require specific cellular microenvironments, or niches, for their culture, is a well-established theory in stem cell biology. As techniques for selectively culturing neural stem cells, neurosphere formation, low-density culture, and high-density culture, etc., were reported, but it is known to be difficult to expand cells in large-scale culture in an undifferentiated state.

Several researchers have attempted the large-scale culture of stem cells. However, human adult neural stem cells are particularly difficult to culture in vitro and also have limited ability to proliferate. For this reason, studies on human adult neural stem cells are at a standstill.

Accordingly the present inventors have conducted studies to overcome the problem of the limited ability of human adult neural stem cells to proliferate, and as a result, have found that, when primarily cultured adult neural stem cells are cultured after genes that can activate the signaling pathways in the neural stem cells have been transfected into the neural stem cell, the ability of the neural stem cells to proliferate is significantly increased, thereby completing the present invention.

SUMMARY OF INVENTION

It is an object of the present invention to provide stem cells in which a gene that activates Notch signaling is introduced, and thus have an excellent ability to proliferate, and a method for producing the stem cells.

Another object of the present invention is to provide a cell therapeutic agent for treating cranial nerve disease, which comprises neural stem cells in which the NICD (Notch intracellular domain) gene is introduced, as an active ingredient.

Still another object of the present invention is to provide stem cells, in which the c-MET gene is introduced and, either in which the HGF (hepatocyte growth factor)-encoding gene is introduced or which are treated with HGF to activate the c-MET/HGF signaling pathway, and a method for proliferating the stem cells.

Still another object of the present invention is to provide a cell therapeutic agent for treating cranial nerve disease, which comprises neural stem cells in which the c-MET gene is introduced as an active ingredient.

Still another object of the present invention is to provide an use of the neural stem cells transfected with the NICD gene for treating or preventing cranical nerve disease.

To achieve the above objects, the present invention provides stem cells having an excellent ability to proliferate, in which a gene that activates Notch signaling is introduced, and a method for proliferating stem cells, the method comprising a step of culturing stem cells transfected with a gene that activates Notch signaling.

The present invention also provides a cell therapeutic agent for treating cranial nerve disease, which comprises neural stem cells or neural crest stem cells in which the NICD (Notch intracellular domain) gene is introduced and Notch signaling is activated, as an active ingredient.

The present invention also provides stem cells having excellent abilities to proliferate, in which the c-MET gene is introduced and, either a HGF (hepatocyte growth factor)-encoding gene is introduced or which are treated with HGF to activate the c-MET/HGF signaling pathway, and a method for proliferating stem cells in which the c-MET/HGF signaling pathway is activated.

The present invention also provides a cell therapeutic agent for treating cranial nerve disease, which comprises neural stem cells or neural crest stem cells in which the c-MET/HGF signaling pathways are activated, as an active ingredient.

Other features and embodiments of the present invention will be more apparent from the following detailed descriptions and the appended claims.

BRIEF DESCRIPTION OF DRAWINGS

FIG. 3 shows that the adult neural stem cells obtained by in vitro culture maintain the ability to differentiate over all passages and shows that early passage cells, passaged 3 times, and late passage cells, passaged 18 times, all differentiated into neural cells.

DETAILED DESCRIPTION OF INVENTION AND PREFERRED EMBODIMENTS

Figure 1:
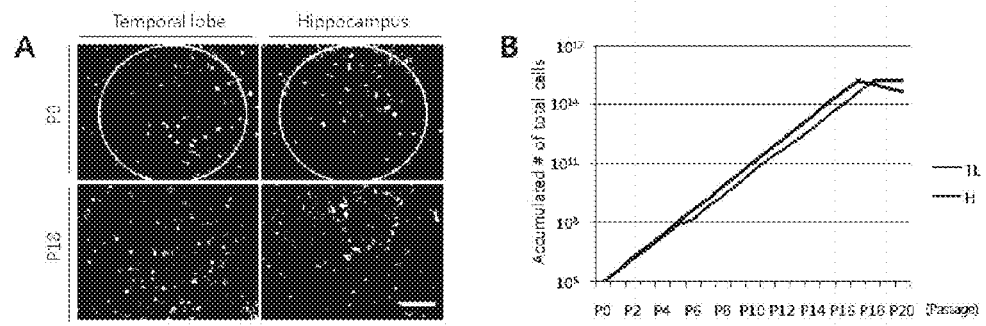
FIG. 1A is a set of photographs of each passages of adult neural stem cells, obtained by primary culture of human temporal lobe tissue and hippocampus tissue (P0: cells at the start of in vitro culture; and P18: cells at passage 18)
FIG. 1B is a graphic diagram showing the accumulated number of adult neural stem cells that proliferated by in vitro passages.

In one aspect, the present invention relates to stem cells having an excellent ability to proliferate, in which a gene that activates Notch signaling is introduced, and a method for proliferating stem cells, comprising a step of culturing said stem cells.

Namely, the present invention relates to stem cells which have an ability to differentiate into various tissues, and thus are effective for cell therapy.

As used herein, the term "stem cells" refers to undifferentiated cells that can differentiate into cells constituting tissues and that start to differentiate under specific differentiation stimuli (environment). Unlike differentiated cells with arrested cell division, stem cells retain the capability of self-renewal through cell division, and thus can proliferate (expand). Moreover, stem cells differentiate into specific cells when differentiation stimuli is applied thereto, and they can also differentiate into different cells under different environments or differentiation stimuli, indicating stem cells have plasticity in differentiation. Such stem cells can be divided, according to the developmental origin thereof, into embryonic stem cells and adult stem cells. In the present invention, it is preferred to use adult stem cells rather than embryonic stem cells that raise serious biological, ethical and legal questions limiting the clinical application thereof.

As used herein, the term "adult stem cell" refers to stem cells extracted from adult body tissues, which are just before differentiating into the cells of a specific organ. Adult stem cells are difficult to proliferate and have a strong tendency to differentiate easily, but can differentiate into tissue-specific progenitor cells in the human body. Adult stem cells can differentiate into cells having various characteristics and have the capability to produce replacement cells for various tissues and organs, including heart, pancreas, nerve tissue, muscle and cartilage.

The above-described adult stem cells can be derived from humans, primates, rodents, and birds. Preferably, the adult stem cells can be derived from mammals, especially mice, rats and humans. For example, these adult stem cells can be obtained from most tissues, including human marrow, fat, umbilical cord blood, blood, liver, skin, gastrointestinal tract, placenta, uterus, brain, pancreas, eye and fetal tissues.

Isolation method of adult stem cells from various human tissues may be performed using a conventional method known in the art, which is suitable for each tissue. For example, a method may be used which comprises treating a collected specific tissue with trypsin solution and/or collagenase to isolate single cells, culturing the single cells in a medium supplemented with suitable amounts of growth factors (e.g., bFGF, EGF, etc.), and isolating adult stem cells from the culture by FACS or according to growth rate.

The most preferred examples of adult stem cells that may be used in the present invention include neural stem cells or neural crest stem cells (NCSCs).

As used herein, the term "neural stem cells" describes a cell that is capable of undergoing greater than 20-30 cell divisions while maintaining the potency to generate both neurons and glia. Preferably, said cells are capable of undergoing greater than 40, more preferably greater than 50, most preferably unlimited such cell divisions. The neural stem cells are by definition multipotent, i.e. they are capable of differentiating into a number of neural cell types (e.g. neurons/glia). The neural stem cells can be obtained by primary culture of the tissues of the Central nervous system (CNS) and the peripheral nervous system (PNS) and differentiate into glial lineage and neural lineage cells under respective sets of conditions (Sally Temple et al. 2001). As used herein, the term "neural crest stem cells (NCSCs)" refers to stem cells that temporally appear during the early embryonic developmental process and are also multipotent stem cells.

It is possible of neural stem cells to be derived from various sources. For example, neural stem cells can be derived from human adult brain tissue, wherein the brain may be any one selected from the group consisting of cerebrum, diencephalon, mesencephalon, cerebellum, medulla oblongata, pons, and spinal cord. Preferably, neural stem cells can be derived from cerebral tissue, such as temporal lobe tissue or hippocampus tissue. Human neural stem cells can be purchased from commercially available sources, and preferably, they can be produced by culturing cells, obtained from human adult brain tissue, in a medium containing neural stem cell growth factors (Example 1).

Particularly, the adult neural stem cells are very difficult to culture in vitro and also have limited ability to proliferate. For this reason, it was difficult to culture neural stem cells in large amounts in an undifferentiated state by conventional culture methods.

In WO 2005/121318 that discloses a method for promoting the symmetric division of neural stem cells, an activator of a signaling pathway downstream of a receptor of the EGF receptor family together with a signaling pathway downstream of a receptor of the FGF receptor family. Unlike this, in the present invention, the above-described problem is solved either by transfecting stem cells with a gene that activates Notch signaling to activate the Notch signaling pathway, or by activating the c-MET/HGF signaling pathway, thereby improving the ability of stem cells (particularly neural stem cells) to proliferate, so that the stem cells can be obtained in large amounts.

The stem cells of the present invention are structurally transfected with a gene that activates Notch signaling, and the Notch signaling pathway is functionally activated.

Notch is the name derived from a gene that induces the excessive growth of the wings of Drosophila during mutation to make Notches in the wings. It is a signaling pathway that plays a crucial role in fast cell-to-cell signaling and amplification in multicellular animals. Notch transduces a signal by cell-to-cell contact through a Delta or Serrate ligand present in the adjacent cell. In the present invention, in order to activate the Notch signaling pathway, a gene that is involved in the Notch signaling pathway is transfected into stem cells.

Transfection of stem cells with a gene that activates Notch signaling means introducing a nucleic acid encoding the gene in the stem cells.

In the present invention, any gene that activates Notch signaling may be used without limitation. Preferably, the NICD gene may be used. As a nucleic acid encoding the NICD, one having a nucleotide sequence encoding the NICD, known in the art, may be used without limitation. Preferably, the gene that activates Notch signaling may have an NICD-encoding sequence comprising a DNA sequence set forth in SEQ ID NO: 1 and may have an amino acid sequence set forth in SEQ ID NO: 2, but the scope of the present invention is not limited thereto. Namely, it may have a nucleotide sequence encoding a functional equivalent of the NICD.

As used herein, the term "functional equivalent" refers to a polypeptide having substantially the same physiological activity as the NICD of the present invention, which has a sequence homology of at least 70%, preferably at least 80%, and more preferably at least 90%, with an amino acid sequence set forth in SEQ ID NO: 2, as a results of the addition, substitution or deletion of amino acids. For example, the polypeptide has a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% with the amino acid sequence set forth in SEQ ID NO: 2. As used herein, the term "substantially the same physiological activity" as the NICD refers to activity that activates the Notch signaling pathway. Also, the nucleic acid encoding the NICD may be prepared by a gene recombination method known in the art.

In the present invention, the gene that activates Notch signaling, for example, an NICD-encoding nucleic acid or a c-MET-encoding nucleic acid, may be operably linked to an expression control sequence and may be inserted into an expression vector. As used herein, the term "expression control sequence" refers to a DNA sequence that regulates the expression of the operably linked nucleic acid in a specific host cell. Such an expression control sequence includes a promoter for initiating transcription, an optional operator sequence for controlling transcription, and a sequence controlling termination of transcription or translation. As used herein, the term "expression vector" refers to a plasmid, viral vector or other vehicles known in the art, into which a nucleic acid encoding the structural gene can be inserted and which can express in the nucleic acid in a host cell. Preferably, the expression vector may be a viral vector.

Examples of the expression vector include, but are not limited to, a retroviral vector, an adenoviral vector, a herpesviral vector, an avipox viral vector, an Epstein-Barr viral vector, a lentiviral vector, etc. In one embodiment of the present invention, a lentiviral vector is used.

The method of preparing lentivirus using a recombinant expression vector according to the present invention may be carried out using a method known in the art. The expression vector comprising the nucleic acid according to the present invention may be introduced into stem cells by any method known in the art, such as transient transfection, microinjection, transduction, cell fusion, calcium phosphate precipitation, liposome-mediated transfection, DEAE dextran-mediated transfection, polybrene-mediated transfection, electroporation, gene gun or other methods for introducing DNA into cells.

In one embodiment of the present invention, neural stem cells in which a gene that activates Notch signaling is introduced may be prepared by, for example, a method comprising the steps of:

(a) preparing a recombinant viral vector comprising a DNA construct containing a nucleic acid encoding NICD;

(b) transfecting the recombinant viral vector into a virus-producing cell line to prepare an NICD-expressing recombinant virus; and (c) infecting neural stem cells with the NICD-expressing recombinant virus.

The virus-producing cell line that is used in the present invention may be a cell line producing a virus corresponding to the viral vector used. For example, if a lentiviral vector is used, 293FT cells producing lentivirus may be used. Then, the recombinant lentiviral vector expressing NICD is transfected into human neural stem cells. In the present invention, the primarily cultured stem cells are preferably transfected with a gene that activates Notch signaling, for example, the NICD gene.

In order to transfect human neural stem cells with lentivirus, any conventional method known in the art may be used. The method may comprise, for example, plating nerve stem cells on a growth factor-containing medium, treating the plated cells with polybrene, and adding to the medium viral particles corresponding to suitable MOI (multiplicity of infection), thus infecting the cells. After the infection, the virus-containing medium may be replaced with a fresh medium for culturing neural stem cells, after which the cells may be cultured.

The stem cell line of present invention, which is overexpressing the gene that activates Notch signaling and prepared as described above, has a very excellent ability to proliferate. Namely, when the Notch signaling pathway is activated by introducing the gene that activates the Notch signaling pathway in the stem cells, the proliferation of the stem cells becomes active. The most preferred examples of the inventive stem cells having an excellent ability to proliferate are neural stem cells or neural crest stem cells in which the NICD gene is introduced and the Notch signaling pathway is activated.

In one embodiment of the present invention, the above-prepared neural stem cells, in which the NICD gene is introduced and the Notch signaling pathway is activated, are characterized in that:

(i) the stem cells express Nestin and CD133, known as neural stem cell-specific marker proteins, and GFAP, an astrocyte-specific marker protein;

(ii) the stem cells do not express Olig2, an oligodendrocyte-specific marker, and Tuj-I protein, a neuron-specific marker;

(iii) the stem cells have a capability to differentiate into any one cell type selected from the group consisting of neutrons, oligodendrocytes and astrocytes;

(iv) the stem cells overexpress NICD;

(v) the Notch signaling pathway is activated.

In one Example of the present invention, the neural stem cells introduced with the NCID gene were cultured, and as a result, it was confirmed that the proliferation of the cells was significantly increased (see Example 4-3).

A medium that may be used in the culture of stem cells according to the present invention may be a suitable medium known in the art depending on the type of stem cell. The medium may contain ascorbic acid, epidermal growth factor (EGF), insulin, antibiotic and FBS (fetal bovine serum). For example, for neural stem cells, a growth factor-containing NBE medium, particularly a medium containing B27™ supplement, N2™ supplement, bFGF and EGF, may be used.

When stem cells are cultured after the transfection with a Notch signaling pathway-activating gene, for example, the NICD gene, the proliferation of the stem cells very actively occurs compared to non-introduced stem cells. Also, the accumulated number of the stem cells significantly changes as the number of passages increases. Preferably, the stem cells are cultured for more than three passages.

Namely, in the inventive method for proliferating stem cells, the stem cells in which a gene that activates the Notch signaling pathway is introduced, so that the stem cells are proliferated in large amounts in an undifferentiated state. Introduction to the stem cells with the Notch signaling pathway-activating gene, for example, the NICD gene, is carried out as described above.

In another aspect, the present invention relates to a cell therapeutic agent comprising, as active ingredients, stem cells in which a gene that activates the Notch signaling is structurally introduced and the Notch signaling is functionally activated.

Particularly, neural stem cells or neural crest stem cells, in which the NICD gene is introduced and Notch signaling pathway is activated, may be used as a cell therapeutic agent for treating cranial nerve diseases. The cranial nerve diseases typically include neurodegenerative diseases. Neurodegenerative diseases or disorders are diseases or medical conditions associated with neuronal loss or dysfunction.

Examples of neurodegenerative diseases or disorders include neurodegenerative diseases, central nervous system injuries or dysfunctions. Neurodegenerative diseases include, for example, Alzheimer's disease or other dementia, multiple sclerosis (MS), schizophrenia, macular degeneration, glaucoma, diabetic retinopathy, peripheral neuropathy, Huntington's disease, amyotrophic lateral sclerosis, and Parkinson's disease. CNS injuries include, for example, cerebrovascular events like strokes (e.g., hemorrhagic strokes, focal ischemic strokes or global ischemic strokes), ocular ischemia, and dural sinus thrombosis; traumatic brain or spinal cord injuries (e.g., injuries caused by a brain or spinal cord surgery or physical accidents); concussion; injury induced by drugs (e.g., chemotherapeutics, recreational drugs, and neuroleptics); coronary artery bypass graft (CABG) surgery; and ischemia at child birth. CNS dysfunctions include, for example, depression, epilepsy, neurosis and psychosis.

As used herein, "treatment" refers to any manner in which the symptoms of a condition are ameliorated or otherwise beneficially altered. Treatment also encompasses retardation of the progress of a disease and improvement, palliation and (partial or complete) remission of symptoms. Also, treatment may mean increased possibility of survival as compared to absence of the treatment. Treatment also encompasses prophylactic measures in addition to therapeutic measures. Cases in need of treatment include those with existing diseases and those where prevention is required. Improvement of diseases means improvement or retardation of symptoms as compared to absence of the treatment.

The present invention also provides the use of stem cells, particularly neural stem cells, a Notch signaling pathway-activating gene, for example, the NICD gene, for preparing a cell therapeutic agent. The inventive stem cells and the effects thereof are as described above.

In another aspect, the present invention relates to stem cells in which the c-MET/HGF signaling pathway is activated, and to a method for proliferating said stem cells, comprising a step of culturing said stem cells.

In the present invention, the activation of the c-MET/HGF signaling pathway can be performed using the following two methods:

First, a method of activating the c-MET/HGF signaling pathway by introducing a gene that activates the c-MET/HGF signaling pathway and the HGF gene in stem cells; and second, a method of activating the c-MET/HGF signaling pathway by treating stem cells, in which the gene that activates the c-MET/HGF signaling pathway is introduced, with a HGF ligand.

Hepatocyte growth factor (HGF), also known as scatter factor (SF), is a multi-functional heterodimeric protein produced predominantly by mesenchymal cells, and is an effector of cells expressing the Met tyrosine kinase receptor. Human Met receptor is also known as "c-MET". HGF mediates a number of cellular activities, when it binds to its cognate receptor. The HGF-Met signaling pathway plays a role in liver re-generation, wound healing, neural regeneration, angiogenesis and malignancies.

HGF binding to Met induces phosphorylation of the intracellular kinase domain resulting in activation of a complex set of intracellular pathways that lead to cell growth, differentiation and migration in a variety of cell types. The HGF/c-MET signaling pathway is involved in multiple biological and physiological functions, including, for e.g., cell growth stimulation (e.g. cell proliferation, cell survival, cell migration, cell morphogenesis) and angiogenesis.

The gene that is used to activate the c-MET/HGF signaling pathway may be the c-MET gene. As a nucleic acid encoding the c-MET, any nucleic acid having a nucleotide sequence encoding the c-MET, known in the art, may be used without limitation.

Preferably, the nucleic acid encoding the c-MET may have a c-MET-encoding sequence comprising a DNA sequence set forth in SEQ ID NO: 5 and may have an amino acid sequence set forth in SEQ ID NO: 6, but the scope of the present invention is not limited thereto. Namely, it may have a nucleotide sequence encoding a functional equivalent of the c-MET.

As used herein, the term "functional equivalent" refers to a polypeptide showing substantially the same physiological activity as the c-MET of the present invention, which has a sequence homology of at least 70%, preferably at least 80%, and more preferably at least 90%, with an amino acid sequence set forth in SEQ ID NO: 6. For example, the polypeptide has a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% with the amino acid sequence of SEQ ID NO: 6. As used herein, the term "substantially the same physiological activity" as the c-MET refers to the activity in which the c-MET receptor protein interacts with the HGF ligand protein to activate the c-MET/HGF signaling pathway. Also, the c-MET-encoding nucleic acid may be prepared by a gene recombination method known in the art.

In one embodiment of the present invention, neural stem cells transfected with a gene that activates the c-MET/HGF signaling pathway may be prepared, for example, by a method comprising the steps of:

(a) preparing a recombinant viral vector comprising a DNA construct containing a c-MET-encoding nucleic acid;

(b) transfecting the recombinant viral vector into a virus-producing cell line to prepare a c-MET-expressing recombinant virus; and (c) infecting neural stem cells with the c-MET-expressing recombinant virus.

The virus-producing cell line can produce a cell line producing a virus corresponding to the viral vector used. For example, when a lentiviral vector is used, 293FT cells producing lentivirus may be used. Then, human neural stem cells are infected with the c-MET-expressing recombinant lentiviral vector. Preferably, in the present invention, the c-MET gene is introduced in primarily cultured stem cells.

In order to infect human neural stem cells with lentivirus, any conventional method known in the art may be used. The method may comprise, for example but not limited to, plating neural stem cells on a growth factor-containing medium, treating the plated cells with polybrene, and adding to the medium viral particles corresponding to suitable MOI (multiplicity of infection), thus infecting the cells. After the infection, the virus-containing medium may be replaced with a fresh medium for culturing neural stem cells, after which the cells may be cultured.

Then, the stem cells transfected with the c-MET gene is treated with HGF (hepatocyte growth factor) ligand protein.

Mature HGF contains two polypeptide chains, α-chain and β-chain. Reported study results suggest that the α-chain contains the c-MET receptor binding domain of HGF. HGF was reported to have a number of different amino acid sequences, including HGF, TCF, SCF, etc. These amino acids are collectively herein referred to as "HGF".

Such HGF ligand protein may be prepared as an aqueous solution formulation so that the cell line is treated with the aqueous solution formulation. Alternatively, it may be inserted into a vector which is then transfected into the cell line. HGF that is used in the present invention may be an HGF-expressing amino acid sequence or a nucleotide sequence encoding it, known in the art.

In the present invention, stem cells in which the c-MET/HGF signaling pathway is activated could be obtained by preparing the HGF ligand protein into an aqueous solution formulation, treating c-MET gene-transfected stem cells with the aqueous solution formulation and culturing the treated stem cells. Alternatively, these stem cells could be obtained by culturing stem cells transfected with both the c-MET gene and the HGF-encoding gene.

A medium that may be used to treat the c-MET gene-introduced stem cells with the HGF ligand protein and to culture the treated stem cells may be a suitable medium known in the art depending on the type of stem cells. The medium may contain ascorbic acid, epidermal growth factor (EGF), insulin, an antibiotic, and FBS (fetal bovine serum). For example, for neural stem cells, a growth factor-containing NBE medium, particularly a medium containing B27™ supplement, N2™ supplement, bFGF and EGF, may be used.

As described above, when stem cells are cultured after transfection with both the c-MET gene and the HGF-encoding gene, or when stem cells are transfected with the c-MET gene, treated with the HGF ligand protein and then cultured, the proliferation of the stem cells very actively occurs compared to non-transfected stem cells. Also, the cumulative increase in the number of the stem cells significantly changes as the number of passages increases. Preferably, the stem cells are cultured for at least three passages.

Namely, in the inventive method for proliferating stem cells, the c-MET gene is introduced in stem cells, so that the c-MET/HGF signaling pathway is activated through the interaction between the c-MET receptor protein and the HGF ligand protein, whereby the stem cells are proliferated in large amounts in an undifferentiated state.

The most preferred examples of the inventive stem cells having an excellent ability to proliferate neural stem cells or neural crest stem cells, in which the c-MET gene is introduced and the c-MET/HGF signaling pathway is activated. The stem cells of the present invention are characterized in that:

(i) the stem cells express Nestin and CD133, known as neural stem cell-specific marker proteins, and GFAP, an astrocyte-specific marker protein;

(ii) the stem cells do not express Olig2, an oligodendrocyte-specific marker, and Tuj-I protein, a neuron-specific marker;

(iii) the stem cells have a capability to differentiate into any one cell type selected from the group consisting of neutrons, oligodendrocytes and astrocytes;

(iv) the stem cells overexpress c-MET; and (v) the c-MET/HGF signaling pathway is activated.

In one embodiment of the present invention, neural stem cells in which the c-MET gene is introduced were treated with the HGF ligand protein to activate the c-MET/HGF signaling pathway. As a result, it was confirmed that the proliferation of the cells was significantly increased compared to a wild-type cell line (see Example 4-3).

In another aspect, the present invention relates to a cell therapeutic agent containing as an active ingredient, stem cells in which the c-MET/HGF signaling pathway is activated.

Particularly, neural stem cells or neural crest stem cells, in which the c-MET/HGF signaling pathway is activated, may be used as a cell therapeutic agent for treating cranial nerve disease.

The stem cells according to the present invention are administered in a manner that permits them to graft or migrate to the intended tissue site and reconstitute or re-generate the functionally deficient area. For example, neural stem cells neural crest stem cells, in which the c-MET/HGF signaling pathway is activated, or neural stem cells neural crest stem cells, in which the NICD gene is introduced and the Notch signaling pathway is activated, can be transplanted directly into parenchymal or intrathecal sites of the central nervous system. Transplants may be done using a single suspension or small aggregates at a density of $1\times10^5$~$1.5\times10^5$ cells per μl. The cell therapeutic agent of the present invention may be administered at a dosage of $10^4$~$10^{10}$ cells/body, and preferably $10^6$~$10^8$ cells/body, once or several times a day.

However, it is to be understood that the actual dosage of the active ingredient should be determined considering various related factors, including a disease to be treated, administration route, the patient's age, sex and weight, and the severity of disease. Thus, the above dosage is not intended to limit the scope of the present invention in any way.

The stem cells according to the present invention can be provided in the form of a pharmaceutical composition for administration into humans. The pharmaceutical composition of the present invention may further comprise a pharmaceutically acceptable carrier. As used herein, the term "pharmaceutically acceptable" refers to non-toxic to a cell or subject that is exposed to the composition. Examples of the carrier that may be used in the present invention include those known in the art, including a buffering agent, a preserving agent, an analgesic, a solubilizing agent, an isotonic agent, a base, an excipient, a lubricating agent, etc. The pharmaceutical composition of the present invention can be prepared in the form of various formulations according to a conventional technical known in the art. For example, for injectable preparations, it can be prepared in the form of unit dosage ampoules or multiple dosage containers. For the general principle of medicinal preparations of the pharmaceutical composition according to the present invention, reference can be made to known literature.

In addition, the present invention provides a method for treating tumor, the method comprising administering to a subject in need thereof an effective amount of stem cells in which the c-MET/HGF signaling pathway is activated, or of stem cells, particularly neural stem cells, in which the Notch signaling pathway is activated. As used herein, the term "effective amount" refers to the amount in which the stem cells of the present invention exhibit a therapeutic effect in the subject. As used herein, the term "subject" means mammals, particularly animals including humans. The subject may be a patient in need of treatment. The stem cells of the present invention may be administered until the desired effect among the above-described effects can be obtained. Also, these stem cells may be administered via various routes according to any conventional method known in the art.

The present invention also provides the use of stem cells, particularly, neural stem cells, in which the c-MET/HGF signaling pathway is activated, for preparing therapeutic agents. The inventive stem cells and the effects thereof are as described above.

Examples

Hereinafter, the present invention will be described in further details with reference to examples. It will be obvious to a person having ordinary skill in the art that these embodiments are merely for illustrative purposes, and the scope of the present invention should not be construed as being limited to the above described embodiments.

Example 1

Preparation of Human Neural Stem Cells 1-1: Isolation and Culture of Human Neural Stem Cells Temporal lobe and hippocampus tissues were obtained from epilepsy patients (Department of Neurosurgery, Samsung Medical Center) by surgical operation.

Within 3 hours after the surgical operation, each tissue was washed with PBS, and then mechanically cut using surgical scissors or blades. The cut tissue was treated at 37° C. for 1 hour or less with an enzymatic solution, prepared by mixing collagenase (0.4 mg/ml, Gibco), DNaseI (0.01-1 mg/ml, Roche), Papain (10 unit/ml, Sigma), D-L-Cystein (400 ng/ml, Sigma) and DNaseI (0.01-1 mg/ml, Roche). Then, the treated tissue was dissociated to single cells using a serum pipette, and then passed through a nylon mesh, thus obtaining single cells.

The single cell suspension was subjected to concentration gradient (Percoll, Sigma) and centrifuged to remove red blood cells and dead cells. The resulting cells were suspended in a Neurobasal-A (Gibco) medium or DMEM:F12 (Gibco) medium containing FBS, B27 supplement (Gibco), N2 supplement (Gibco), bFGF (R&D) and EGF (R&D). Then, the cells were cultured in a cell culture plate pre-treated with poly-L-ornithine (Sigma), thereby obtaining primarily cultured neural stem cells.

1-2: Passage Culture

The neural stem cells obtained in Example 1-1 were passaged at intervals of about 10 days. The passage culture was performed in the following manner.

The medium was removed from the cell culture plate, and the cells were treated with 2 ml of 0.05% trypsin/EDTA (T/E, Gibco) and incubated in a 5% $CO_2$ incubator at 37° C. Then, to stop the action of trypsin, 2.5 ml of 1% FBS-containing medium was added thereto and mixed therewith. The cell suspension was transferred into a 15 me conical tube (Falcon). It was centrifuged to remove the supernatant. The cells were re-suspended in 1 ml of Neurobasal-A medium (Gibco) or DMEM:F12 medium (Gibco), and then the number of cells was measured. Then, the cell suspension containing about $10^5 \sim 5 \times 10^5$ cells was transferred onto a fresh culture plate containing 50% of the prior medium, and 50 ng/ml bFGF and 50 ng/ml EGF were added thereto. Then, the cells were incubated in a 5% $CO_2$.

FIG. 1A is a set of photographs showing the adult neural stem cells of the isolated human temporal lobe and hippocampus tissues at various passages.

The accumulated number of the neural stem cells that proliferated during passages was measured. As a result, as shown in FIG. 1B, a cell growth curve having a constant slope was obtained.

1-3: Analysis of Characteristics of Human Neural Stem Cells

The neural stem cells obtained as described above were fixed with 4% paraformaldehyde (PFA, Sigma) or acetone/methanol, and then permeabilized with PBS containing 0.05% Triton X-100 (Sigma) for 15 minutes. Then, the tissue was blocked with 5% normal horse serum/1% normal goat serum (Vector Lab.) at room temperature for 1 hour.

Next, the cells were washed several times PBS containing 0.01% triton X-100 (Sigma) and treated with a combination of anti-CD133 (Abcam), anti-musashi (Chemicon), anti-nestin (Abcam or Millipore), anti-Sox2 (R&D), anti-Sox9 (Abcam), anti-Sox10 (Abcam), anti-Vimentin (Millipore), anti-GFAP (Sigma or Abcam), anti-Olig2 (Millipore), anti-O4 (Chemicon), and anti-Tuj-I (Millipore). Then, the cells were incubated at 4° C. overnight.

Then, the cells were treated with secondary antibodies (anti-mouse-488(BD), anti-mouse-594(BD), anti-rabbit-488 (BD), anti-rabbit-594(BD), anti-rat-488(BD), and anti-rat-594(BD)) corresponding the above primary antibodies. Finally, the cells were nucleus-stained with DAPI (Sigma), and the expression of final fluorescence was observed with a fluorescence microscope (Axiovert, Zeiss).

Figure 2:
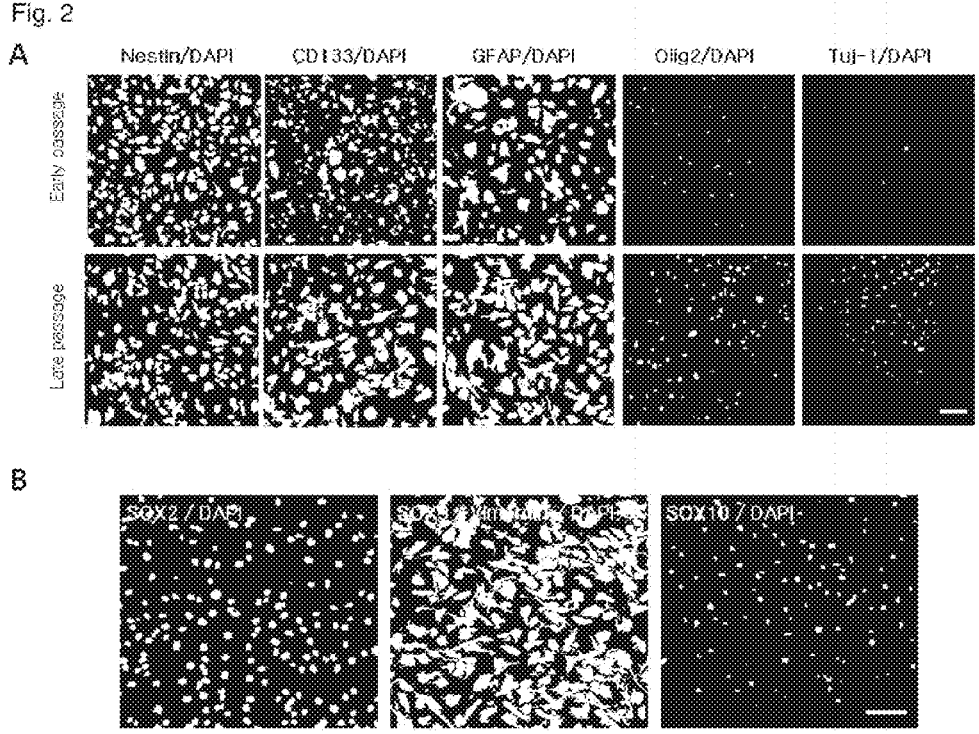
FIG. 2 shows the results of examining the expression of human adult neural stem cell-specific marker proteins by immunocytochemistry (A: Nestin+/CD133+/GFAP+/Olig2−/Tuj-1−; and B: Sox2+/Sox9+/Vimentin+/Sox10−).

As a result, the expression of Nestin and CD133, known as neural stem cell-specific marker proteins, and the astrocyte-specific marker GFAP, was observed, and it was observed that the oligodendrocyte-specific marker Olig2 and the neuron-specific marker Tuj-I were not expressed (FIG. 2A), and Sox2, Sox9 and Vimentin were strongly expressed (FIG. 2B). This suggests that the characteristics of the neural stem cells were maintained over all the passages.

1-4: Examination of the Ability of Human Neural Stem Cells to Differentiate

Figure 3:
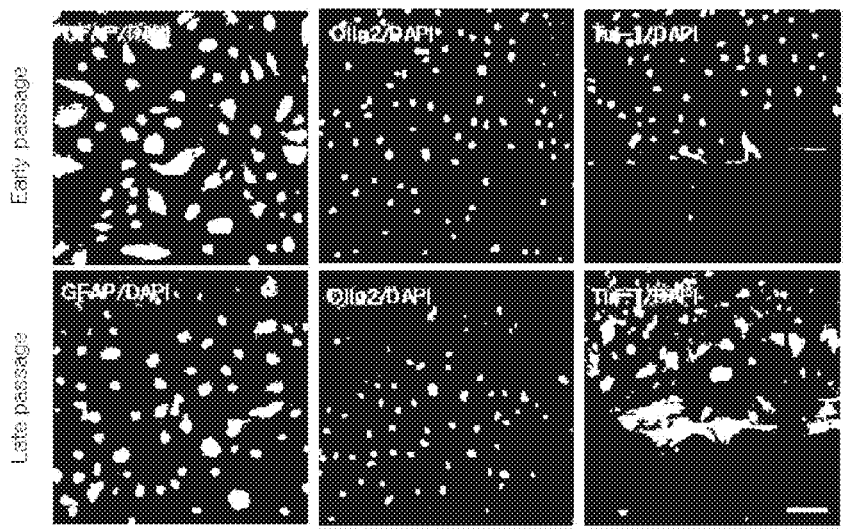
FIG. 3 shows the results of examining the expressions of lower neural cell-specific marker proteins by immunocytochemistry in order to examine the ability of human adult neural stem cells to differentiate.

In order to confirm whether the adult neural stem cells obtained as described above have the ability to differentiate into lower neural stem cells and whether the differentiation ability is maintained during the subculture period, the cells were suspended in Neurobasal-A (Gibco) or DMEM:F12 (Gibco) medium containing FBS, B27 supplement (Gibco) and N2 supplement (Gibco). Then, the cells were cultured in a cell culture plate pre-treated with Poly-L-Ornithine (Sigma) and Laminin (Sigma). Then, the cells were cultured in a 10% FBS-containing Neurobasal-A (Gibco) medium or DMEM: F12 (Gibco) medium or a Neurobasal-A (Gibco) medium containing nerve growth factor (R&D), IBMX and dcAMP for 1-2 weeks, thereby inducing the differentiation thereof. The expression of lower neural cell-specific marker proteins in these differentiated cells was analyzed by immunocytochemistry. As a result, it could be seen that the differentiation ability of the cells was maintained over all the passages (FIG. 3).

Example 2

Construction of Recombinant Lentivirus Expressing NICD (Notch Intracellular Domain)

2-1: Preparation of Recombinant Viral Vector

First, the NICD of SEQ ID NO: 1 was amplified from neural stem cells by RT-PCR. Total RNA was extracted from the neural stem cells of Example 1 using a Rneasy kit (Qiagen), and then treated with reverse transcriptase Superscript III (Invitrogen) to synthesize cDNA which was used as a temperature for PCR amplification. The EmGFP gene (Invitrogen) was amplified by PCR from a pLenti6.3/V5-GW/ EmGFP vector (Invitrogen). The primers used in the PCR amplification of the two genes contained a CACC sequence in order to initiate the expression of amino acids in the lentivirus vector. Specifically, the primers had the following sequences:

```
                                     (SEQ ID NO: 3)
Forward primer:   CACC ATG CGG CGG CAG CAT GGC CAG (SEQ ID NO: 4)
Reverse primer:   TTA CTT GAA GGC CTC CGG AAT G
```

The PCR reaction was performed under the following conditions: initial denaturation at 94° C. for 5 min; 15 cycles of denaturation at 94° C. for 1 min, annealing at 60° C. for 30 sec, and extension at 72° C. for 3 min; and final extension at 72° C. for 10 min. The amplified PCR product was cloned into a pENTR-D-TOPO vector (Invitrogen).

For stable expression of the introduction gene in the neural stem cells, the promoter region of the human ubiquitin C (UbC) gene was amplified by PCR from a pLenti6/UbC/V5-DEST vector (Invitrogen). The primers used in the PCR amplification contained ClaI and SpeI restriction enzyme sequences for each cloning. The above-amplified promoter region of the UbC gene was cloned into a pGEM-T easy vector (Promega), and then treated with ClaI and SpeI restriction enzymes, thus obtaining a gene fragment. Also, the CMV promoter region of a pLenti7.3/V5-DEST vector (Invitrogen) was removed using the same restriction enzymes, thus obtaining a vector fragment. Then, the gene fragment and the vector fragment were treated with ligase (Promega), thus obtaining an expression vector inserted with the UbC promoter.

To insert a reporter gene, the vector was inserted with a KpnI restriction enzyme to obtain a vector fragment, and a pSuper-retro vector (Oligoengine) was treated with the same restriction enzyme to obtain a gene fragment. Then, the gene fragment and the vector fragment were treated with Ligase (Promega), thereby obtaining an expression vector inserted with the UbC promoter. The NICD and EmGFP genes were transferred into the obtained expression vector using LR clonase (Invitrogen), thereby obtaining a final expression vector.

The structure of the lentivirus vector constructed as described above is shown in FIG. 4-A.

2-2: Preparation of Recombinant Lentivirus Expressing NICD (1) Production of Lentivirus As a virus packaging cell line, a 293FT cell line (Invitrogen) was used. The 293FT cell line was co-transfected with the NICD-overexpressing vector, constructed in Example 2-1, and three virus packaging-associated vectors (pLP-1, pLP-2, and pLP/VSVG; Invitrogen), using Lipofectamine reagent (Invitrogen), thereby inducing the production of virus.

(2) Collection of Lentivirus Particles

The cell culture of the virus-producing cell line obtained as described above was collected up to 72 hours after the co-transfection. The supernatant culture was collected 6 times while replacing the medium with a fresh medium at 12-hour intervals. The collected virus was stored at 4° C.

(3) Titration of Lentivirus Particles

The above-collected virus-containing supernatant culture was passed through a 0.22 μm syringe filter to remove the cell suspension. In a 24-well plate, 293FT cells, cultured at a cell concentration of $1 \times 10^4$ cells/ml, were treated with 6 μg/ml of polybrene (Sigma) and infected with the prepared virus, diluted serially diluted at 10×, 1×, 0.5×, 0.25×, 0.125×, and 0.0625×.

Then, the number of EGFP-expressing cells was counted by FACS assay (FACS Calibur., BD), or the concentration at which the ratio of the virus particles to the number of cells reached 1:1 was selected through puromycin antibiotic selection. Herein, the number of virus particles was quantified based on the concentration.

Example 3

Infection of Neural Stem Cell by NICD-Expressing Recombinant Lentivirus and Selection of Infected Cell Line In a 24-well plate pretreated with poly-L-ornithine, neural stem cells cultured at a cell concentration of $1 \times 10^4$ cells/ml were treated with 6 μg/ml of polybrene (Sigma). Then, the cells were infected with the NICD-expressing recombinant lentivirus of Example 2 at $1 \times 10^3$ transducing unit (TU).

At 3 hours after the start of the infection, the prior virus-containing medium was replaced with a fresh medium for culturing neural stem cells, and then the cells were cultured for 12 hours. After the culture, 1 μg/ml of Puromycin antibiotic (Sigma) was added thereto, and antibiotic selection was performed for 5 days.

Example 4

Examination of Characteristics of Neural Stem Cells in which NICD Gene is Introduced 4-1: Examination of Neural Stem Cells in which NICD Gene is Introduced For the neural stem cell line transfected with the NICD-expressing recombinant lentivirus, selected in Example 3, the characteristics of the neural stem cells transfected with the NICD gene were analyzed in the same manner as in Example 1-2.

Figure 4:
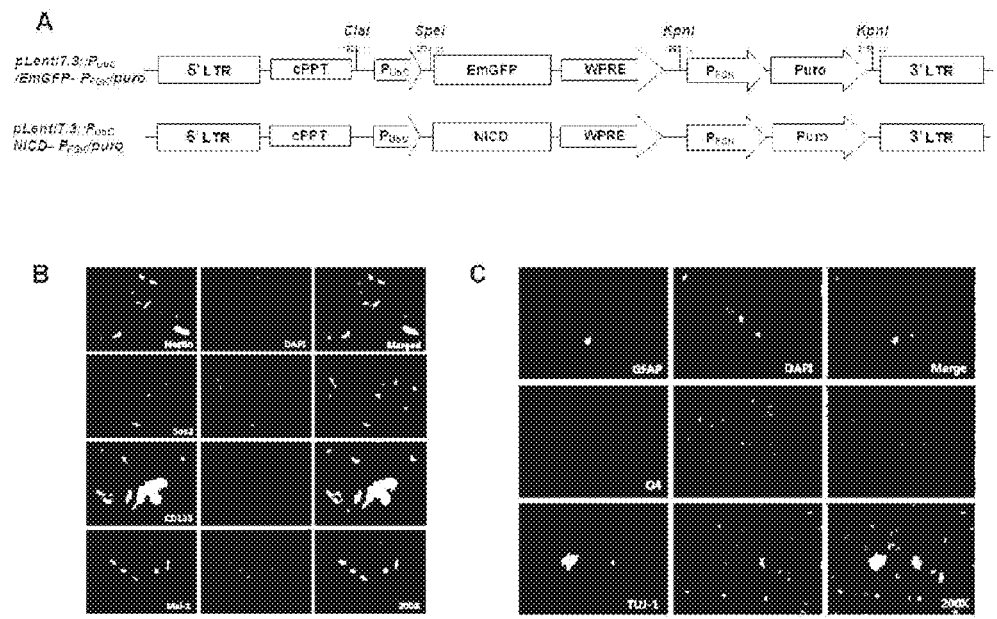
FIG. 4A shows the structure of a lentivirus vector constructed to transfect the NICD gene into adult neural stem cells.
FIG. 4B shows the results of examining the expression of neural stem cell-specific marker proteins in the NICD gene-transfected adult neural stem cells by immunocytochemistry (neural stem cell-specific markers)
FIG. 4C shows the results of examining the ability of these cells to differentiate into lower neural stem cells (astrocyte-, oligodendrocyte- and neuron-specific markers).

As a result, as shown in FIG. 4, Musashi, Nestin, Sox2 and CD133, known as neural stem cell-specific marker proteins, were strongly expressed (FIG. 4-B).

4-2: Examination of the Ability of NICD Gene-Introduced Neural Stem Cells to Differentiate In order to confirm whether the NICD-overexpressing adult neural stem cells obtained as described above have the ability to differentiate into lower neural cells and whether the ability of the cells to differentiate is maintained for passages, the cells were suspended in a Neurobasal-A culture (Gibco) or DMEM:F12 culture (Gibco) containing FBS, B27 supplement (Gibco) and N2 supplement (Gibco), and then were cultured in a cell culture plate, pretreated with poly-L-ornithine (Sigma) and Laminin (Sigma). Then, the cells were cultured for 1-2 weeks in a 10% FBS-containing Neurobasal-A medium (Gibco) or DMEM:F12 medium (Gibco) or in a Neurobasal-A medium (Gibco) containing nerve growth factor (R&D), IBMX and dcAMP, thereby inducing the differentiation of the cells. The expression of lower neural cell-specific marker proteins in the differentiated cells was analyzed by immunohistochemistry in the same manner as described in Example 1-3. As a result, it could be seen that the ability of the stem cells to differentiate was maintained over all the passages (FIG. 4C). In FIG. 4C, GFAP: an astrocyte-specific marker; O4: an oligodendrocyte-specific marker; and Tuj-I: neuron-specific marker.

4-3: Examination of the Ability of NICD Gene-Introduced Neural Stem Cells to Proliferate The NICD-expressing recombinant lentivirus-transfected neural stem cells selected in Example 3 were cultured in a 24-well plate, pretreated with poly-L-ornithine, at a cell concentration of $5 \times 10^3$ cells/ml. Then, the cells were treated with the same amount of CCK-8 reagent (Dojindo) and cultured in a 5% $CO_2$ cell incubator at 37° C. for 2-4 hours. The supernatant was transferred to a 96-well plate, and then the absorbance at a wavelength of 460 nm was measured using a micro well plate reader.

Figure 5:
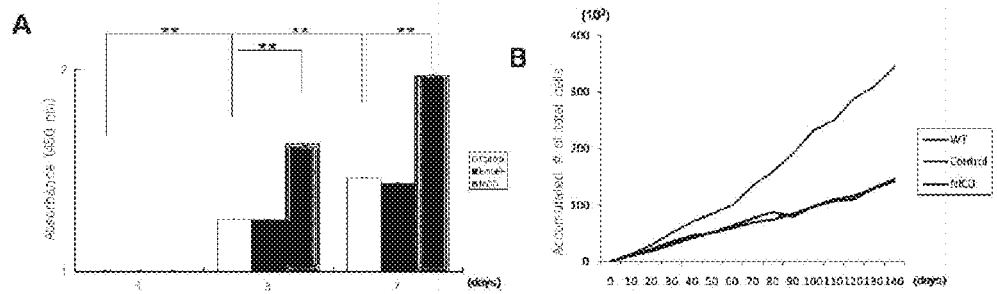
FIG. 5A shows the results of examining the proliferation ability of NICD gene-transfected adult neural stem cells by CCK assay.
FIG. 5B shows the accumulated number of total cells that proliferated by subculture.

As a result, as shown in FIG. 5A, the proliferation of the NICD-expressing cell line was significantly increased compared to the wild-type cell line and the EmGFP-expressing cell line. Then, the neural stem cells were subcultured while the proliferation thereof was observed. The number of the cells proliferated was counted, and the results are shown in FIG. 5-B. As can be seen therein, the accumulated number of total cells was significantly higher in the NICD-expressing cell line than in the control group.

Such results indicate that activation of the Notch signaling pathway by introduction of the NICD gene significantly increases the ability of the adult neural stem cells to proliferate. This suggests that the adult neural stem cells can be proliferated in large amounts so that they can be used as cell therapeutic agents.

Example 5

Construction of c-MET-Expressing Recombinant Lentivirus 5-1: Preparation of Recombinant Viral Vector First, a c-MET gene of SEQ ID NO: 5 was amplified from neural stem cells by RT-PCR. Total RNA was extracted from the neural stem cells of Example 1 using Rneasy kit (Qiagen), and then treated with reverse transcriptase Superscript III (Invitrogen) to synthesize cDNA which was then used as a template for PCR amplification. The EmGFP gene (Invitrogen) was amplified from a pLenti6.3/V5-GW/EmGFP vector (Invitrogen) by PCR. The primers used for the amplification of the two genes contained a CACC sequence in order to initiate the expression of amino acids in a lentivirus vector. Specifically, the primers had the following sequences:

```
                                        (SEQ ID NO: 7)
Forward primer:    CACCGGTACCATGAAGGCCCCCGCTGTGC (SEQ ID NO: 8)
Reverse primer:    GCGGCCGCCTATGATGTCTCCCAGAAGGAGG
```

The PCR reaction was performed under the following conditions: initial denaturation at 94° C. for 5 min; 15 cycles of denaturation at 94° C. for 1 min, annealing at 60° C. for 30 sec, and extension at 72° C. for 3 min; final extension at 72° C. for 10 min. The amplified PCR product was cloned into a pENTR-D-TOPO vector (Invitrogen).

Also, for stable expression of the introduced gene in the neural stem cells, the promoter region of the human ubiquitin C (UbC) gene was amplified by PCR from a pLenti6/UbC/V5-DEST vector (Invitrogen). The primers used in this PCR amplification contained ClaI and SpeI restriction enzyme sequences for easy cloning. The above-amplified promoter region of the UbC gene was cloned into a pGEM-T easy vector (Promega), and then treated with ClaI and SpeI restriction enzymes, thus obtaining a gene fragment. Also, the CMV promoter region of a pLenti7.3/V5-DEST vector (Invitrogen) was removed using the same restriction enzymes, thus obtaining a vector fragment. Then, the gene fragment and the vector fragment were treated with ligase (promega), thus obtaining an expression vector inserted with the UbC promoter.

To insert a reporter gene, the vector was treated with a KpnI restriction enzyme to obtain a vector fragment, and a pSuper-retro vector (Oligoengine) was treated with the same restriction enzyme to obtain an antibiotic expression promoter and a gene fragment. Then, the gene fragment and the vector fragment were treated with ligase (promega), thus obtaining an expression vector inserted with the UbC promoter. The c-MET and EmGFP genes were transferred into the obtained expression vector using LR clonase (Invitrogen), thereby obtaining a final expression vector.

The structures of the c-MET-expressing lentivirus vector and EmGFP-expressing lentivirus vector prepared as described above are shown in FIG. 6A.

5-2: Preparation of c-MET-Expressing Recombinant Lentivirus Vector

As a virus packaging cell line, the 293FT cell line (Invitrogen) was used. The 293FT cell line was co-transfected with the c-MET-overexpressing vector, constructed in Example 2-1, and with three virus packaging-associated vectors (pLP-1, pLP-2, and pLP/VSVG; Invitrogen), using lipofectamine reagent (Invitrogen), thus inducing the production of virus. Also, the EmGFP-expressing recombinant vector was used in the same manner, thus inducing the production of virus.

The collection and titration of lentivirus particles were performed in the same manner as Examples 2-2 and 2-3.

Example 6

Infection of Neural Stem Cells by c-MET-Expressing Recombinant Lentivirus and Selection of Infected Cell Line Neural stem cells were cultured in a 24-well plate, pretreated with poly-L-ornithine, at a cell concentration of $1 \times 10^4$ cells/ml. The cultured cells were treated with 6 μg/ml of polybrene (Sigma). Then, the cells were infected with the c-MET-expressing recombinant lentivirus, prepared in Example 2, at 1×10³ transducing unit (TU).

At 3 hours after the start of the infection, the prior virus-containing medium was replaced with a fresh medium for culturing neural stem cells, and then the cells were cultured for 12 hours. After the culture, 1 ug/ml of Puromycin antibiotic (Sigma) was added to the cells, and antibiotic selection was performed for 5 days.

Example 7

Examination of Characteristics of Neural Stem Cells in which c-MET Gene is Introduced 7-1: Examination of Characteristics of Neural Stem Cells in which c-MET Gene is Introduced For the neural stem cell line transfected with the c-MET-expressing recombinant lentivirus, selected in Example 5, the characteristics of the neural stem cells transfected with the c-MET gene were examined in the manner as described in Examples 1 and 2.

Figure 6:
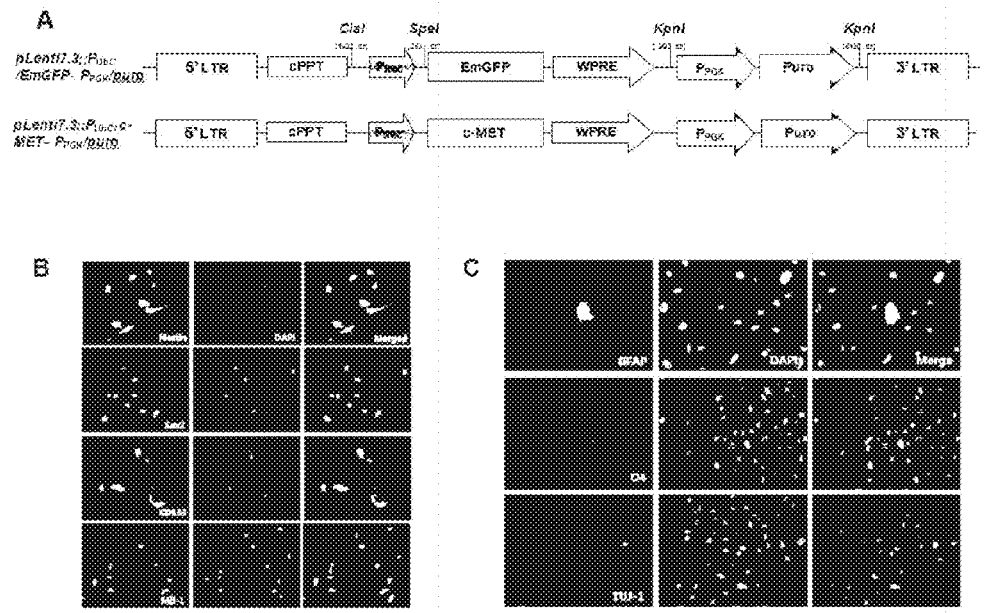
FIG. 6A shows the structure of a lentivirus vector constructed to transfect the c-MET gene into adult neural stem cells.
FIG. 6B shows the results of examining the expression of neural stem cell-specific marker proteins in the c-MET gene-transfected adult neural stem cells by immunocytochemistry (neural stem cell-specific markers)
FIG. 6C shows the results of examining the ability of these cells to differentiate into lower neural stem cells (astrocyte-, oligodendrocyte- and neuron-specific markers).

As a result, as shown in FIG. 6, Musashi, Nestin, Sox2 and CD133, known as neural stem cell-specific marker proteins, were strongly expressed (FIG. 6B).

7-2: Examination of the Ability of c-MET Gene-Introduced Neural Stem Cells to Differentiate In order to confirm whether the c-MET-overexpressing adult neural stem cells obtained as described above have the ability to differentiate into lower neural cells and whether the differentiation ability is maintained during the subculture period, the cells were suspended in a Neurobasal-A medium (Gibco) or DMEM:F12 medium (Gibco) containing FBS, B27 supplement (Gibco) and N2 supplement (Gibco), and were cultured in a cell culture plate pretreated with poly-L-ornithine (Sigma) and laminin (Sigma). Then, the cells were cultured for 1-2 weeks in a 10% FBS-containing Neurobasal-A culture (Gibco) or DMEM:F12 culture (Gibco) or a Neurobasal-A medium (Gibco) containing nerve growth factor (R&D), IBMX and dcAMP, thereby inducing the differentiation of the cells. The expression of lower neural cell-specific marker proteins in the differentiated cells was analyzed by immunohistochemistry in the same manner as in Example 1-3. As a result, it was found that the ability of the cells to differentiate was maintained over the subculture period (FIG. 6C). In FIG. 6C, GFAP: an astrocyte-specific marker; O4: an oligodendrocyte-specific marker; and Tuj-I: a neuron-specific marker.

7-3: Examination of the Ability of c-MET Gene-Introduced Neural Stem Cells to Proliferate For the neural stem cells transfected with the c-MET-expressing recombinant lentivirus or with the EmGFP-expressing recombinant lentivirus, selected in Example 5, HGF was added to a cell culture medium at a concentration of 10-1,000 μg/ml for each cell group. Then, the cells were cultured in a 24-well plate, pretreated with poly-L-ornithine, at a cell concentration of 5×10³ cells/ml in a 5% $CO_2$ incubator at 37° C. To measure the ability of the cell to proliferate, the medium was treated with the same amount of CCK-8 reagent (Dojindo). After 2-4 hours of cell culture, the culture supernatant was transferred to a 96-well plate, and the absorbance at a wavelength of 460 nm was measured using a microwell plate reader.

Figure 7:
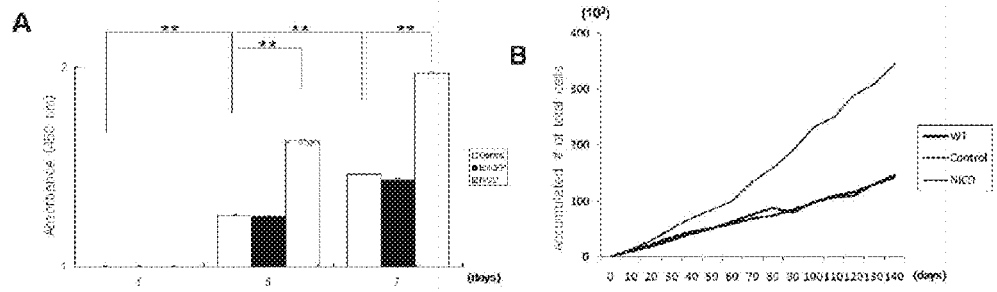
FIG. 7A shows the results of examining the proliferation ability of c-MET-transfected adult neural stem cells by CCK assay.
FIG. 7B shows the accumulated number of total cells that proliferated by subculture.

As a result, as shown in FIG. 7-A, the proliferation of cells was significantly higher in the c-MET-expressing cell line than in the wild type and EmGFP-expressing cell lines.

Then, the neural stem cells were subcultured while the proliferation thereof was observed. The number of cells proliferated was counted, and the results are shown in FIG. 7-B. As can be seen therein, the accumulated number of total cells was significantly larger in the c-MET-expressing cell line than in the control group.

From such results, it could be seen that activation of the c-MET/HGF signaling pathway significantly increased the ability of the adult neural stem cells to proliferate. This suggests that adult neural stem cells can be proliferated in large amounts so that they can be used as cell therapeutic agents.

In the above Examples, the stem cells in which the c-Met/HGF signaling pathway was activated were prepared by treating the c-Met gene-transfected cells with the HGF ligand. However, it will be obvious to a person of ordinary skill in the art that the stem cells in which the c-Met/HGF signaling pathway was activated can be prepared by introducing the c-Met gene and the HGF gene at the same time and expressing the HGF gene in the cells. Introduction of the HGF gene can be achieved using retrovirus, adenovirus, herpes virus, Epstein-Barr virus, lentivirus or the like as a vector, in a manner similar to introduction of the c-MET gene.

INDUSTRIAL APPLICABILITY

According to the present invention, as a result of activating the Notch signaling pathway or the c-MET/HGF signaling pathway, stem cells having an excellent ability to proliferate can be produced in large amounts. Particularly, neural stem cells which have been difficult to culture in vitro can be proliferated in large amounts, and thus the neural stem cells will be more useful for the preparation of cell therapeutic agents for treating cranial nerve diseases.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

SEQUENCE LISTING FREE TEXT

Attach electronic file

The invention claimed is:

1. Isolated stem cells in which a c-MET gene and a hepatocyte growth factor (HGF)-encoding gene are introduced into the stem cells to activate a c-MET/HGF signaling pathway, wherein the stem cells are neural stem cells or neural crest stem cells.

2. The stem cells of claim 1, wherein the c-MET gene consists of a sequence comprising the nucleotide sequence set forth in SEQ ID NO: 5.

3. The stem cells of claim 1, wherein the neural stem cells or the neural crest stem cells are obtained from human adult brain tissue.

4. The stem cells of claim 3, wherein the human adult brain tissue is temporal lobe tissue or hippocampus tissue.

5. The stem cells of claim 1, wherein the genes are introduced by a viral vector.

6. The stem cells of claim 5, wherein the viral vector is one selected from the group consisting of retrovirus, adenovirus, herpes virus, Epstein-Barr virus, and lentivirus.

* * * * *